(12) United States Patent  
Takahashi et al.

(10) Patent No.: US 10,456,093 B2
(45) Date of Patent: Oct. 29, 2019

(54) MEDICAL IMAGE DIAGNOSTIC APPARATUS

(71) Applicant: HITACHI, LTD., Tokyo (JP)

(72) Inventors: Kentaro Takahashi, Tokyo (JP); Hirohisa Izumo, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 387 days.

(21) Appl. No.: 14/765,986

(22) PCT Filed: Jan. 29, 2014

(86) PCT No.: PCT/JP2014/051927
§ 371 (c)(1),
(2) Date: Aug. 5, 2015

(87) PCT Pub. No.: WO2014/123042
PCT Pub. Date: Aug. 14, 2014

(65) Prior Publication Data
US 2016/0007936 A1 Jan. 14, 2016

(30) Foreign Application Priority Data

Feb. 6, 2013 (JP) ................................. 2013-021661

(51) Int. Cl.
*A61B 5/00* (2006.01)

(52) U.S. Cl.
CPC .......... *A61B 5/7475* (2013.01); *A61B 5/7278* (2013.01); *A61B 5/7435* (2013.01); *A61B 5/7445* (2013.01); *A61B 5/704* (2013.01); *A61B 2560/0475* (2013.01)

(58) Field of Classification Search
CPC ... A61B 5/7475; A61B 5/7278; A61B 5/7435; A61B 5/7445; A61B 5/055; A61B 5/0555; A61B 5/704; A61B 5/748; A61B 6/03; A61B 6/032; A61B 6/035; A61B 6/0492; A61B 6/463; A61B 6/467; G01R 33/20; G09B 23/28; G09B 23/30; G06T 7/0012
USPC .......... 434/262, 267, 269, 270; 382/128–132
See application file for complete search history.

(56) References Cited

U.S. PATENT DOCUMENTS

| | | | |
|---|---|---|---|
| 6,049,622 A * | 4/2000 | Robb | G06T 19/003 382/128 |
| 6,603,494 B1 * | 8/2003 | Banks | A61B 5/055 600/410 |
| 2007/0109294 A1 * | 5/2007 | Gotman | A61B 6/00 345/418 |

(Continued)

FOREIGN PATENT DOCUMENTS

| | | |
|---|---|---|
| JP | 9-94247 A | 4/1997 |
| JP | 10-234719 A | 9/1998 |
| JP | 2003-135439 A | 5/2003 |

(Continued)

*Primary Examiner* — Carolyn A Pehlke

(57) ABSTRACT

Reference part selection objects indicating the position and direction of the reference part of an object are displayed at a plurality of positions together with a body position setting image 3A showing the positional relationship between a scanning unit 10 and the object. Then, when a reference part selection object at an arbitrary position is selected, a body position corresponding to the selected object is set as a scanning condition. In addition, the display is switched to a body position setting image corresponding to the selected object.

13 Claims, 14 Drawing Sheets

(56) References Cited

U.S. PATENT DOCUMENTS

2008/0188735 A1\* 8/2008 Furudate ................ A61B 5/055
                                                      600/407

FOREIGN PATENT DOCUMENTS

| JP | 2007-267773 A | 10/2007 |
|----|---------------|---------|
| JP | 2010-35814 A  | 2/2010  |

\* cited by examiner

FIG.7
(a) 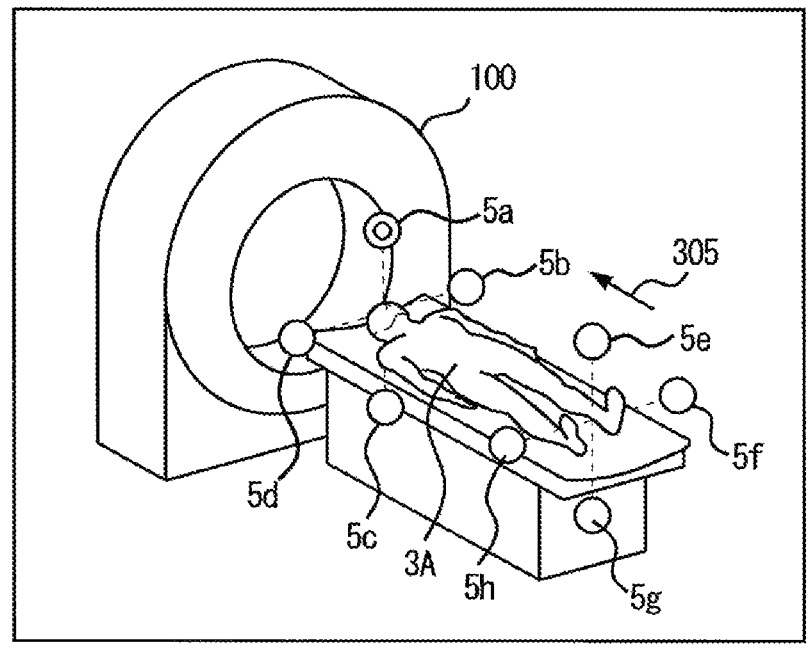
(b) 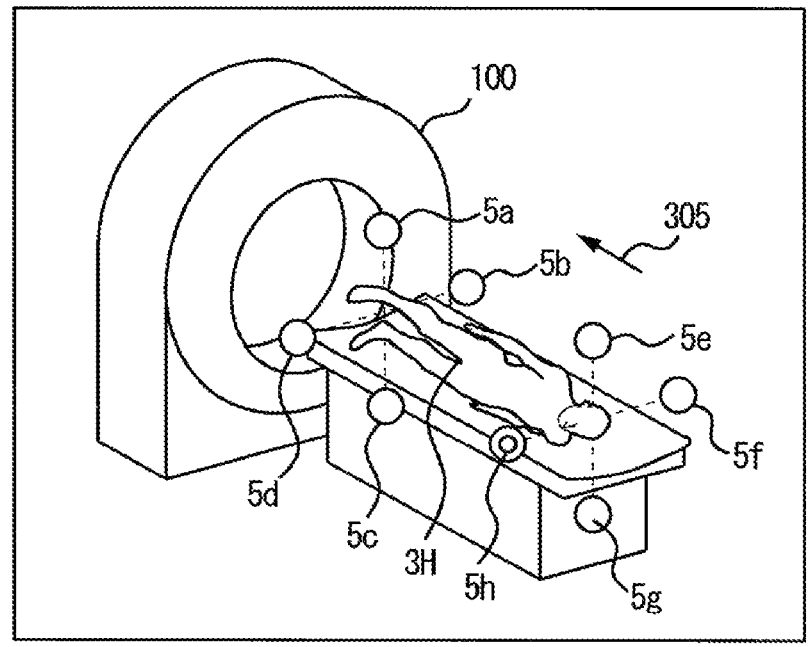

FIG.9
(a)
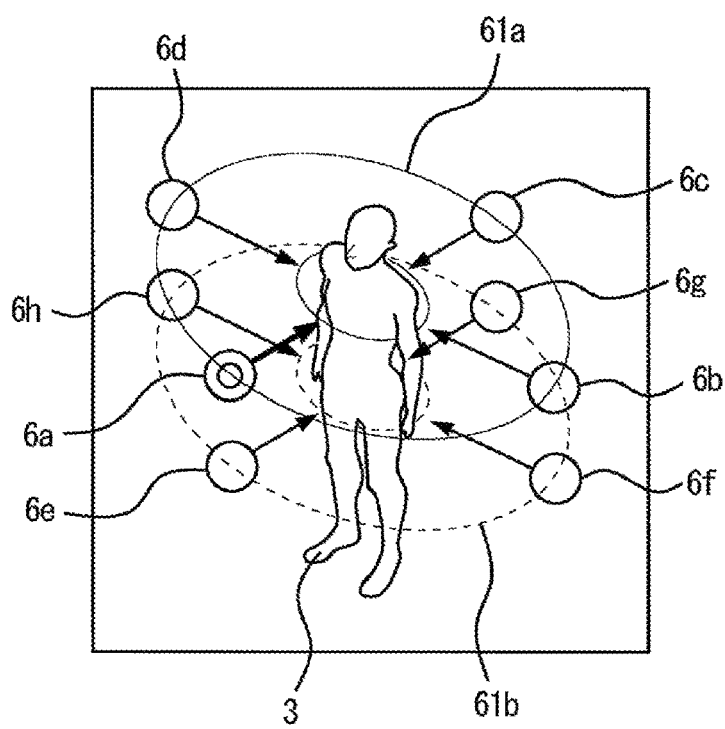
(b)
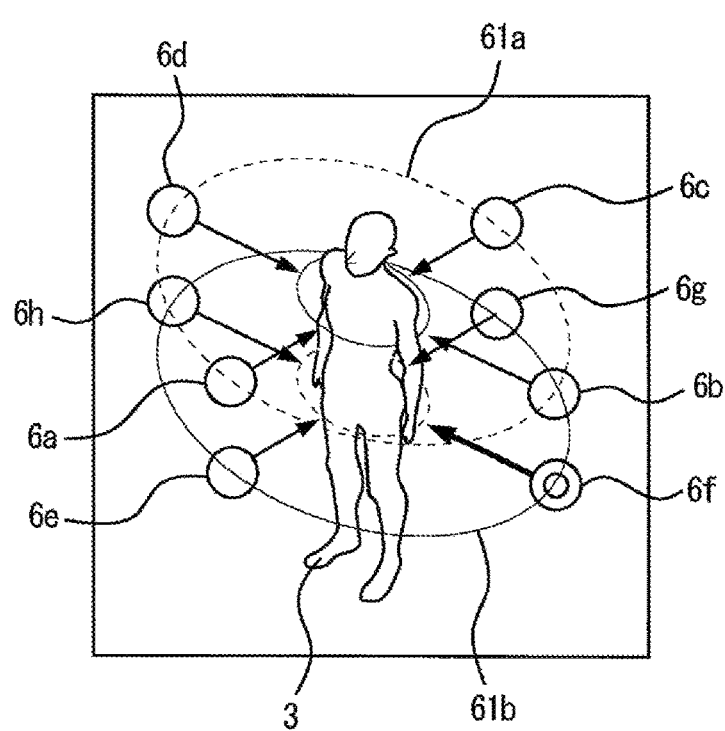

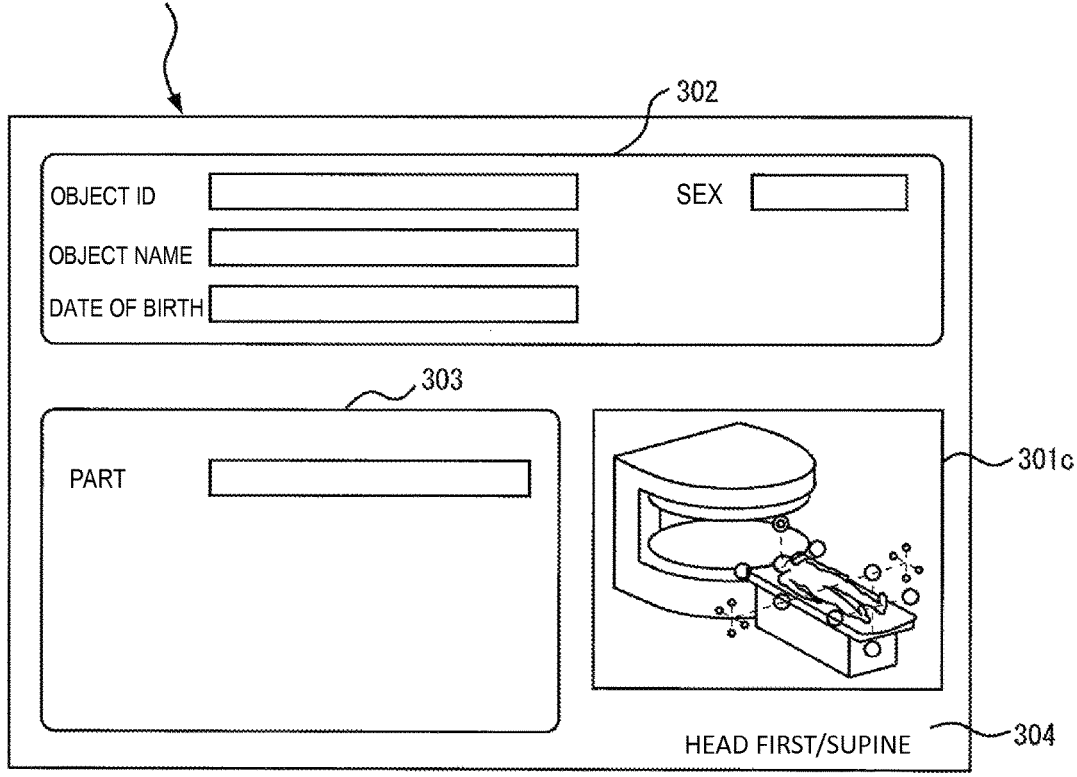

MEDICAL IMAGE DIAGNOSTIC APPARATUS

TECHNICAL FIELD

The present invention relates to a medical image diagnostic apparatus, and in particular, relates to a body position setting in the medical image diagnostic apparatus.

BACKGROUND ART

For example, in the examination using a medical image diagnostic apparatus, such as an X-ray CT apparatus, the scanning conditions are set through the console placed in the operating room. As one of the scanning conditions, there is a setting regarding the body position of an object. Examples of the setting regarding the body position of an object include a setting (body position setting) regarding the lying direction of the object, such as supine, prone, lying on the left side, and lying on the right side, and a direction setting to specify whether the direction of the object with respect to the scanner is a head (Head First) or feet (Feet First).

Display screens at the time of body position setting are illustrated in Patent Literature 1. On these display screens, a body position designation region and a direction designation region are provided in different areas. Selection buttons of "supine", "prone", "lying on the left side", and "lying on the right side" are displayed in the body position designation region. Selection buttons of "Head First" and "Feet First" are displayed in the direction designation region. The operator sets a body position by operating the selection button in the body position designation region, and sets a direction by operating the selection button in the direction designation region.

CITATION LIST

Patent Literature

[PTL 1] JP-A-2010-35814

SUMMARY OF INVENTION

Technical Problem

In the body position setting method disclosed in Patent Literature 1, the operator needs to perform an operation of at least two clicks in order to set both the body position and the direction. In addition, on the display screen for body position setting proposed in Patent Literature 1, the positional relationship between the medical image diagnostic apparatus and the object has not been drawn. Therefore, it has been difficult for the operator to intuitively understand the relative positional relationship between the medical image diagnostic apparatus and the object.

The present invention has been made in view of the above problems, and it is an object of the present invention to provide a medical image diagnostic apparatus in which the positional relationship between an object and a scanning unit or the direction of scanning is easily understood and a body position setting can be easily performed with a small number of operations.

Solution to Problem

In order to achieve the above-described object, the present invention provides a medical image diagnostic apparatus including: a console that inputs and display scanning conditions; a scanning unit that scans an object according to the scanning conditions; an image processing unit that collects measurement data acquired by the scanning unit and generates a medical image based on the measurement data; a storage unit that stores body position setting images, which show body positions of the object at the time of an examination together with a positional relationship with the scanning unit, for a plurality of body positions; a display control unit that displays one of the body position setting images stored in the storage unit on a display device; an object control unit that displays a plurality of reference part selection objects for selecting a position and direction of a reference part of the object in the body position setting image and controls an operation of each reference part selection object; an input unit that inputs an instruction to select the reference part selection object; and a body position setting unit that sets the body position of the object as the scanning conditions according to the position and direction of the reference part selection object selected through the input unit.

Advantageous Effects of Invention

According to the present invention, it is possible to provide a medical image diagnostic apparatus in which the positional relationship between an object and a scanning unit or the body position and direction of the object is easy to be understood and a body position setting can be easily performed with a small number of operations.

BRIEF DESCRIPTION OF DRAWINGS

FIG. 7 is a diagram for explaining the transition of the display state of a body position setting area 301 of the scanning condition setting screen 300.

FIG. 9 is a diagram for explaining the transition of the display state of a body position setting area 301b of the scanning condition setting screen 300b.

FIG. 14 is an example of the scanning condition setting screen 300c (third embodiment).

DESCRIPTION OF EMBODIMENTS

Figure 1:
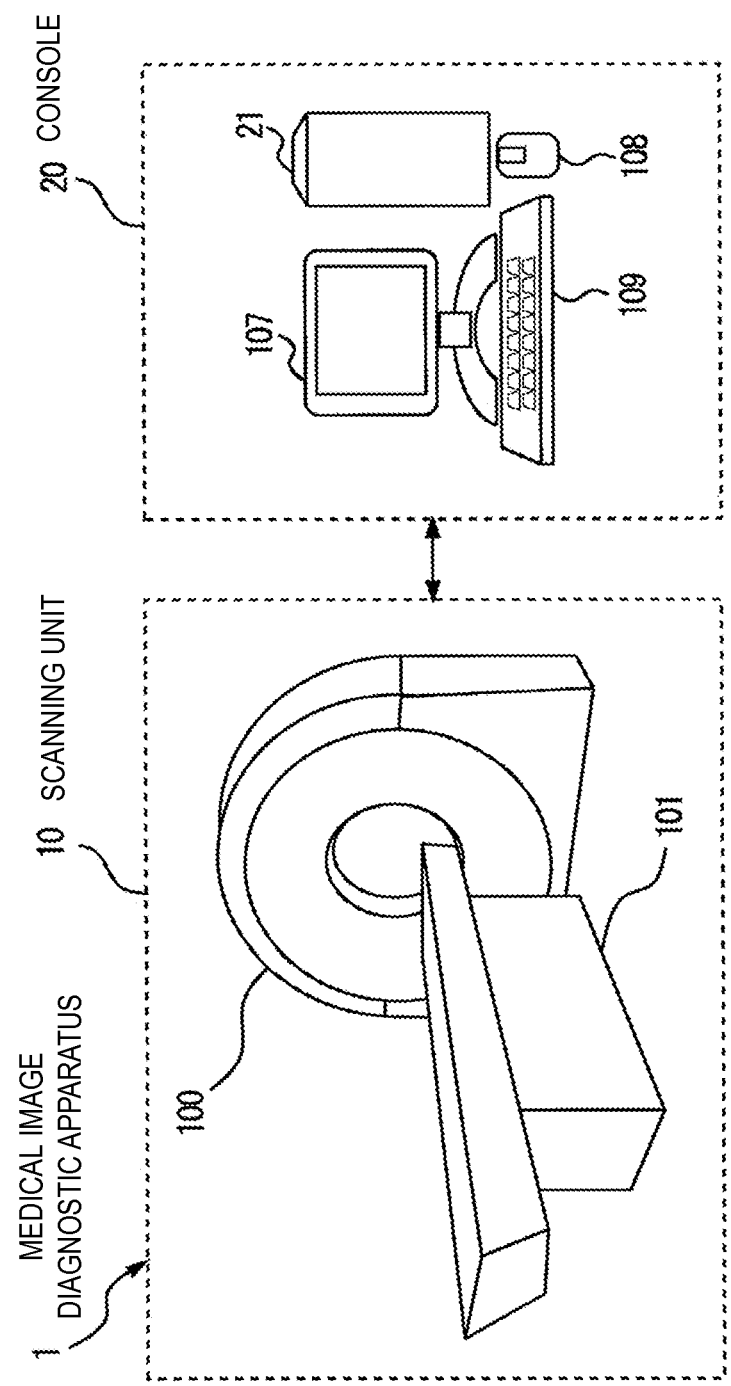
FIG. 1 is an external view showing the entire configuration of the medical image diagnostic apparatus 1.

A medical image diagnostic apparatus according to the present embodiment includes: a console that inputs and display scanning conditions; a scanning unit that scans an object according to the scanning conditions; an image processing unit that collects measurement data acquired by the scanning unit and generates a medical image based on the measurement data; a storage unit that stores body position setting images, which show body positions of the object at the time of an examination together with a positional relationship with the scanning unit, for a plurality of body positions; a display control unit that displays one of the body position setting images stored in the storage unit on a display device; an object control unit that displays a plurality of reference part selection objects for selecting a position and direction of a reference part of the object in the body position setting image and controls an operation of each reference part selection object; an input unit that inputs an instruction to select the reference part selection object; and a body position setting unit that sets the body position of the object as the scanning conditions according to the position and direction of the reference part selection object selected through the input unit.

The display control unit reads a body position setting image, which corresponds to the position and direction of the reference part selection object selected through the input unit, from the storage unit, and displays the read body position setting image by switching a body position setting image displayed on the display device to the read body position setting image.

The body position setting image is a perspective view.

The reference part is the head of the object.

A plurality of body position setting images are stored in the storage unit when the object at the same body position is viewed from different points of view. The display control unit reads a body position setting image, which corresponds to a positional relationship between the scanning unit and a display device that displays the body position setting images, from the storage unit, and displays the read body position setting image.

The body position setting image is displayed on a display device provided in the console in an operating room.

The body position setting image is displayed on a display device provided in the scanning unit.

In the body position setting image, the object placed on a bed is drawn.

In the body position setting image, the object in a standing position is drawn.

Body position setting images, in which directions of a body axis of the object with respect to the scanning unit are different, are stored in the storage unit. The object control unit further displays a body axis selection object for selecting a direction of a body axis in the body position setting image and controls an operation of the body axis selection object.

Hereinafter, embodiments of the present invention will be described in detail with reference to the diagrams.

First Embodiment

Figure 2:
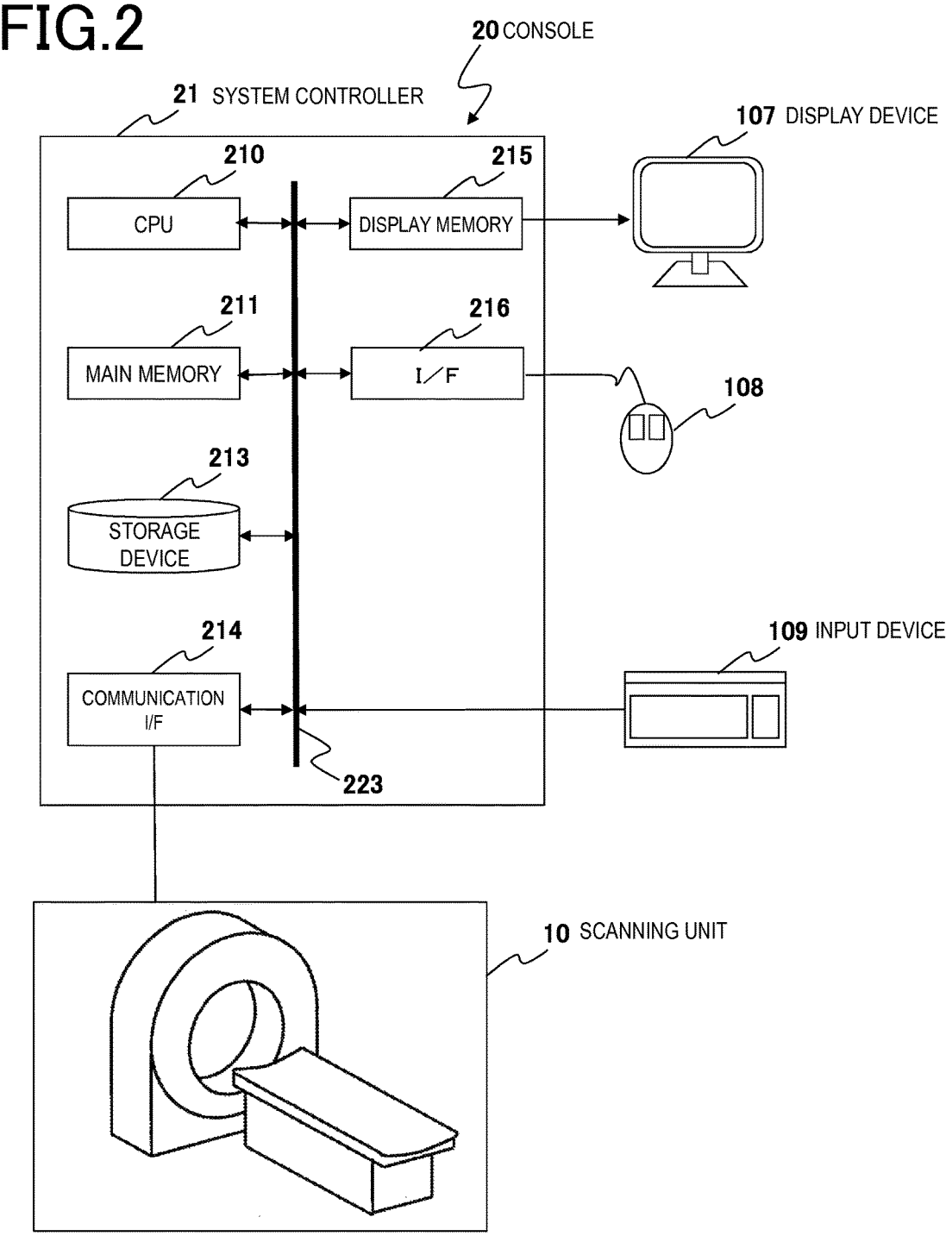
FIG. 2 is a diagram for explaining the internal configuration of a console 2.

First, the hardware configuration of a medical image diagnostic apparatus 1 of the present invention will be described with reference to FIGS. 1 and 2. In the first embodiment, an X-ray CT apparatus will be described as an example of the medical image diagnostic apparatus 1. In addition, the medical image diagnostic apparatus 1 is not limited to the X-ray CT apparatus, and may be any apparatus that performs scanning in a state in which an object is placed on the bed, such as an MRI apparatus.

The medical image diagnostic apparatus 1 roughly includes a scanning unit 10 and an operating console 20. For example, the scanning unit 10 is disposed in the scanning room, and the operating console 20 is disposed in the operating room.

The scanning unit 10 is configured to include a gantry 100 and a bed device 101. When the medical image diagnostic apparatus 1 is an X-ray CT apparatus, the gantry 100 includes an X-ray generator, an X-ray detector, a data collection device, a driving device, and the like.

The bed device 101 includes a top plate on which an object is placed and each moving mechanism for moving the top plate in each direction of an object body axis direction, a horizontal direction, and a vertical direction. Each moving mechanism moves the top plate according to the control signal input from the operating console 20. Therefore, the object is carried into a predetermined position in the X-ray irradiation space of the gantry 100, and is removed therefrom.

The operating console 20 is a computer that performs setting of various scanning conditions and the like, generation of a medical image based on measurement data measured by the scanning unit 10, and display of a medical image. The operating console 20 includes a display device 107, an input device 109, a mouse 108, a system controller 21, and the like.

The system controller 21 includes a central processing unit (CPU) 210, a main memory 211, a storage device 213, a communication interface (communication I/F) 214, a display memory 215, and an interface (I/F) 216 with an external device, such as the mouse 108, and the respective units are connected to each other through a bus 223.

The CPU 210 loads a program stored in the main memory 211 or the storage device 213 to a work memory area on a RAM of the main memory 211 and executes the program, and performs driving control of each unit connected through the bus 223, thereby realizing various kinds of processing performed by the system controller 21.

The main memory 211 is configured to include a read only memory (ROM), a random access memory (RAM), and the like. The ROM permanently stores a program, such as a booting program or BIOS of a computer, data, and the like. The RAM temporarily stores a program, data, and the like loaded from the ROM, the storage device 213, and the like, and has a work area used when the CPU 210 performs various kinds of processing.

The storage device 213 is a storage device that performs reading/writing of data from/into a hard disk drive (HDD) or other recording media, and stores a program executed by the CPU 210, data required to execute the program, an operating system (OS), and the like. As the program, a control program equivalent to the OS or an application program is stored. Each program code is read by the CPU 210 when necessary and is moved to the RAM of the main memory 211, thereby being executed as various kinds of means.

The communication I/F 214 includes a communication controller, a communication port, and the like for mediating communication with the scanning unit 10. The communication I/F 214 performs control of communication with the scanning unit 10, an image database, and other computers through a network (not shown), such as a LAN.

The I/F 216 is a port for connection with a peripheral device, and performs transmission and reception of data to and from the peripheral device. For example, a pointing device, such as the mouse 108 or a stylus pen, may be connected through the I/F 216.

The display memory 215 is a buffer in which the display data input from the CPU 210 is temporarily accumulated. The accumulated display data is output to the display device 107 at a predetermined timing.

The display device 107 is formed by a display device, such as a liquid crystal panel or a CRT monitor, and a logic circuit that cooperates with the display device to execute display processing, and is connected to the CPU 210 through the display memory 215. The display device 107 displays the display data accumulated in the display memory 215 under the control of the CPU 210.

The input device 109 is an input device, such as a keyboard, for example, and outputs to the CPU 210 various kinds of instructions or information input by the operator. The operator operates the system controller 21 interactively using an external device, such as the display device 107, the input device 109, and the mouse 108. The input device 109 may be a touch panel formed integrally with the display device 107.

Figure 3:
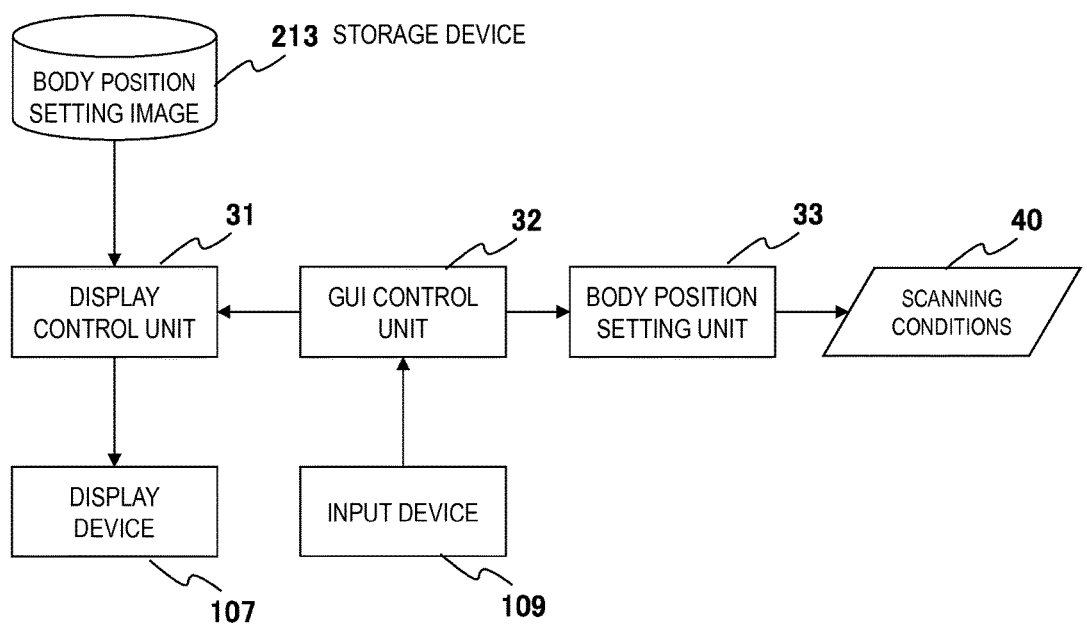
FIG. 3 is a functional block diagram according to the body position setting of a medical image diagnostic apparatus 1.

Next, the functional configuration of the medical image diagnostic apparatus 1 will be described with reference to FIG. 3.

The system controller 21 of the medical image diagnostic apparatus 1 includes a display control unit 31, a GUI control unit 32, and a body position setting unit 33 as a functional configuration regarding a body position setting. A plurality of body position setting images are stored in the storage device 213 of the system controller 21. The body position setting image is an image showing the body position and direction of the object at the time of an examination together with the positional relationship with the scanning unit 10 (gantry 100).

Figure 5:
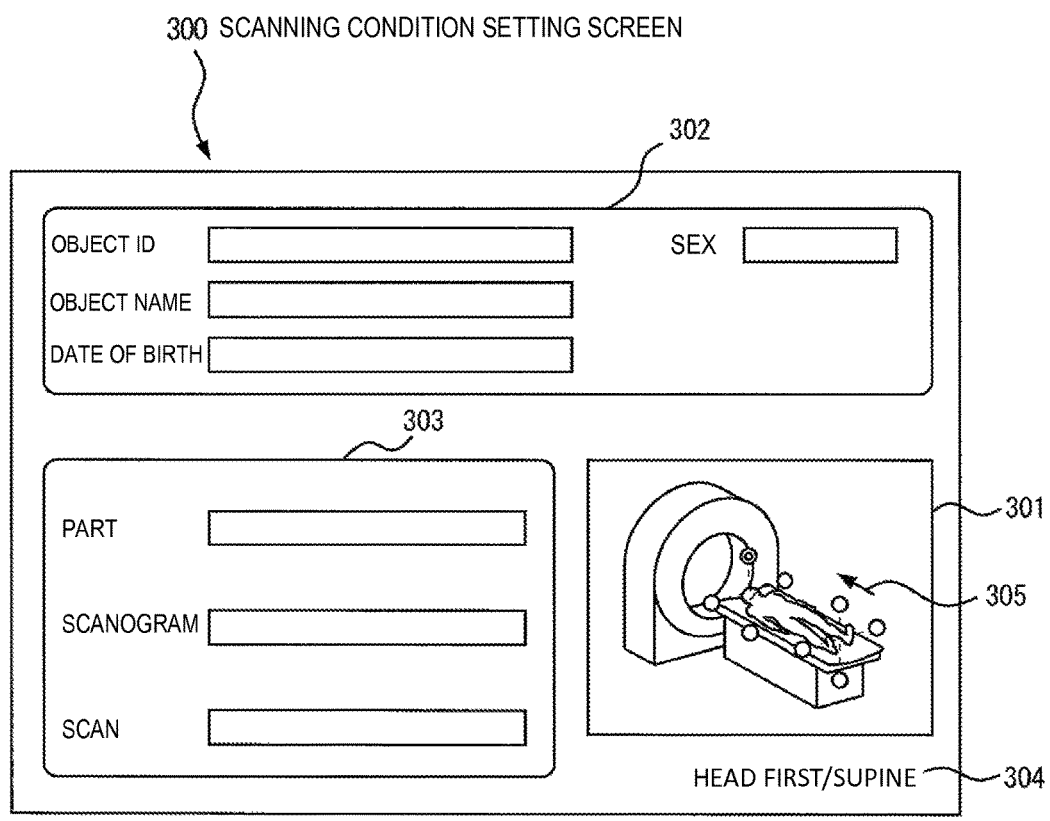
FIG. 5 is an example of a scanning condition setting screen 300 (first embodiment).

The display control unit 31 displays a scanning condition setting screen 300 shown in FIG. 5 on the display device 107 during the scanning condition setting in the medical image diagnostic apparatus 1. The display control unit 31 reads one of body position setting images 3A to 3H (refer to FIG. 6) stored in the storage device 213, and displays the read image on the scanning condition setting screen 300.

The GUI control unit 32 controls reference part selection objects 5a to 5h (refer to FIG. 7) in the body position setting image displayed on the scanning condition setting screen 300. The reference part selection objects 5a to 5h are graphical user interface (GUI) for selecting the position and direction of the object drawn within the body position setting image. The reference part selection objects 5a to 5h are displayed as marks or figures having predetermined shapes. The reference part selection objects 5a to 5h are disposed in a direction in which a predetermined reference part of the object directly faces the reference part selection objects 5a to 5h. That is, the reference part selection objects 5a to 5h are disposed at a plurality of positions where the reference part can be taken at the time of scanning. It is preferable that the reference part of the object is, for example, ahead (face). However, other parts may be set as a reference part. Setting the head (face) as a reference part is preferable since it is easy to understand four directions such as upper, lower, right and left directions sensibly.

The body position setting images 3A to 3H and the reference part selection objects 5a to 5h will be described later.

The input device 109 receives the selection of the reference part selection objects 5a to 5h by the operator. The input device 109 generates a reference part selection signal corresponding to the selected reference part selection object, and transmits the reference part selection signal to the GUI control unit 32. The input device 109 may be the mouse 108 or the like.

The GUI control unit 32 switches the reference part selection objects 5a to 5h to the display state of "selected" or "not selected" according to the reference part selection signal input from the input device 109. In addition, the GUI control unit 32 transmits the reference part selection signal to the display control unit 31 and the body position setting unit 33.

The display control unit 31 reads a corresponding body position setting image from the storage device 213 according to the reference part selection signal, and displays the body position setting image by switching the image displayed on the display device 107 to the body position setting image. That is, when a certain reference part selection object is selected by the operator, an image is switched so that the reference part (head) directly faces the selected object.

The body position setting unit 33 sets the body position and direction of the object as scanning conditions 40 according to the reference part selection signal.

Next, a body position setting method of the medical image diagnostic apparatus 1 of the first embodiment will be described with reference to FIGS. 4 to 7.

Figure 4:
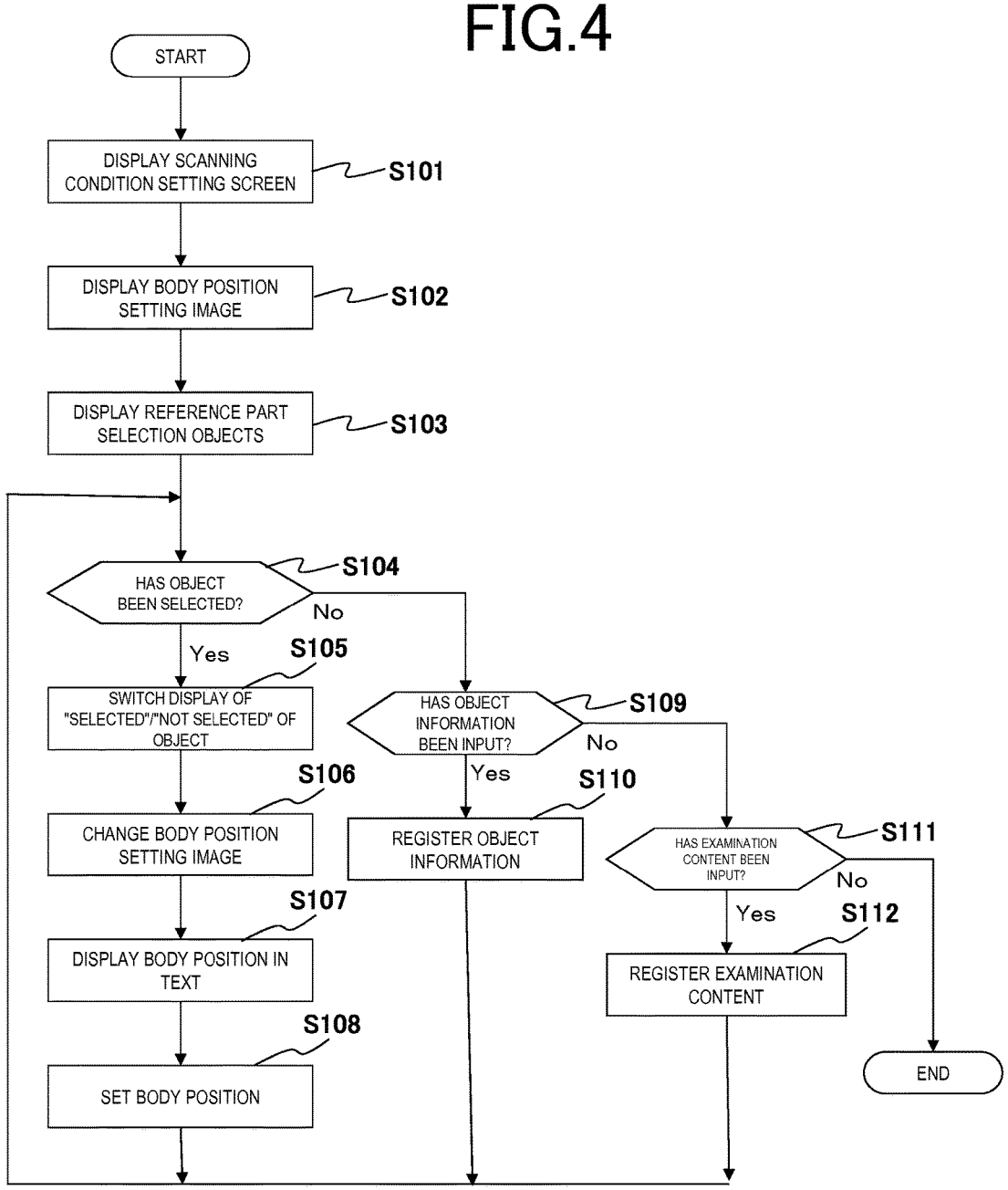
FIG. 4 is a flowchart showing the flow of the body position setting process (first embodiment).

Prior to executing the process of the flowchart shown in FIG. 4, first, the operator guides an object so that the object enters the scanning room. In addition, the operator places the object on the bed. In this case, the body position of the object is a body position and direction according to the examination purpose. Then, the top plate is moved into the scanning space by moving the bed. Then, the operator performs an operation for body position setting and alignment with respect to the medical image diagnostic apparatus 1. The body position setting and the alignment are performed while operating the scanning condition setting screen 300 displayed on the display device 107. Although various kinds of scanning condition settings are performed on the scanning condition setting screen 300, the body position setting that is a part of the scanning condition settings will be described in the present embodiment.

The system controller 21 displays the scanning condition setting screen 300 on the display device 107 (step S101).

For example, as shown in FIG. 5, a body position setting area 301, an object information input area 302, and an examination content setting area 303 are provided on the scanning condition setting screen 300. In addition, a body position display area 304, in which the body position and the direction that are currently selected are displayed, may be provided near the body position setting area 301.

The body position setting area 301 is an area for setting the body position and direction of the object placed on the bed 101. Patterns of the body position (lying direction) include supine, prone, lying on the left side, and lying on the right side, for example. Patterns of the direction include "head first" in which the head is placed on the gantry 100 side and "feet first" in which the feet are placed on the gantry 100 side. Thus, when there are body positions (lying directions) of four patterns and directions of two patterns, a total of eight body position patterns are present.

Figure 6:
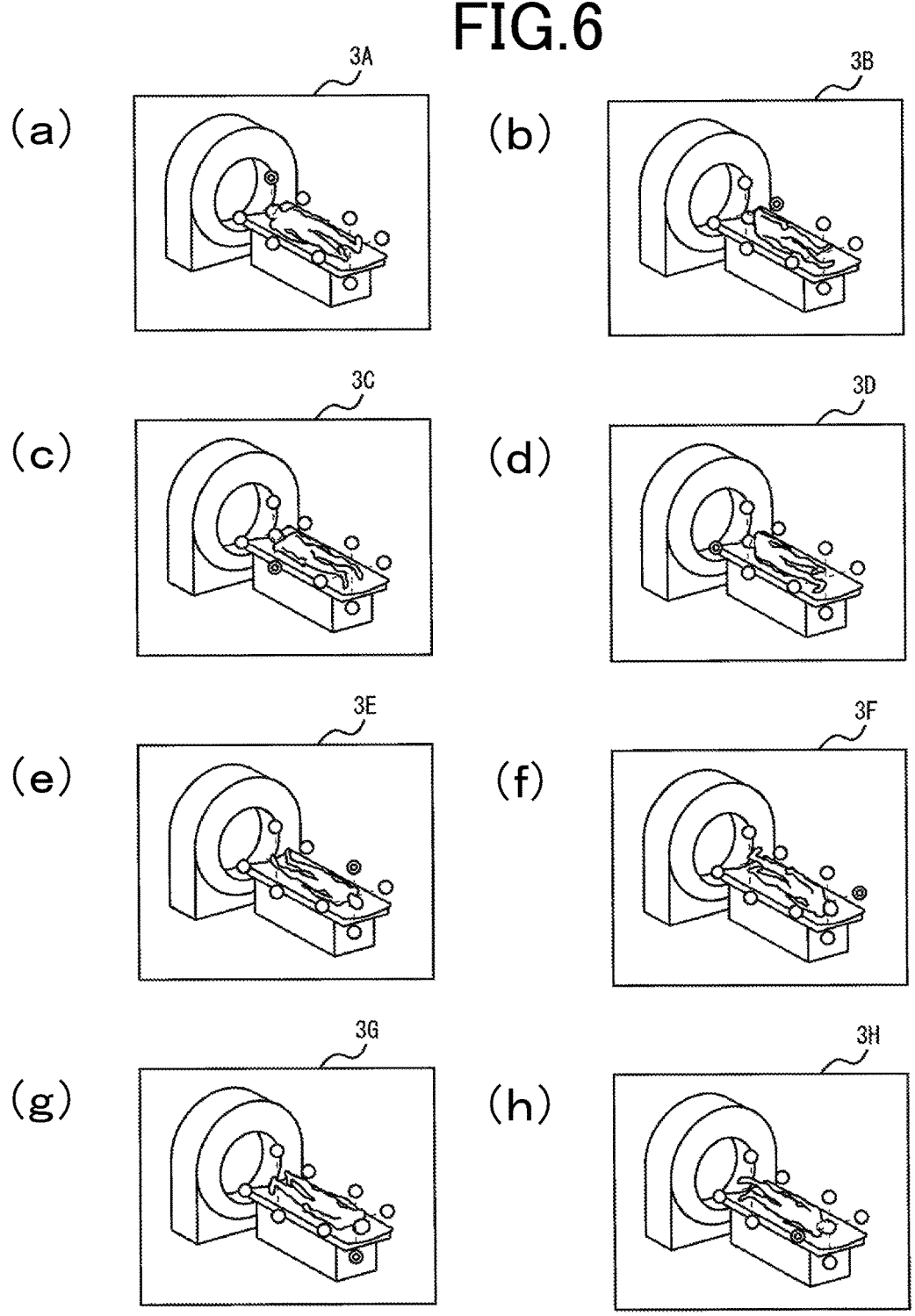
FIG. 6 is an example of a body position setting image stored in a storage device 213.

Body position setting images of all body position patterns that can be taken in the medical image diagnostic apparatus 1 are stored in the storage device 213. FIG. 6 shows examples of the body position setting images 3A to 3H stored in the storage device 213.

FIG. 6(a) is a body position setting image 3A showing "headfirst/supine", FIG. 6(b) is a body position setting image 3B showing "head first/lying on the left side", FIG.

6(*c*) is a body position setting image 3C showing "head first/prone", FIG. 6(*d*) is a body position setting image 3D showing "head first/lying on the right side", FIG. 6(*e*) is a body position setting image 3E showing "feet first/supine", FIG. 6(*f*) is a body position setting image 3F showing "feet first/lying on the right side", FIG. 6(*g*) is a body position setting image 3G showing "feet first/prone", and FIG. 6(*h*) is a body position setting image 3H showing "feet first/lying on the left side".

All of the body position setting images 3A to 3H described above show the body position and direction of the object at the time of an examination together with the positional relationship with the scanning unit (gantry 100). In addition, a perspective view is preferable for the body position setting images 3A to 3H. By displaying the body position in a perspective view, the positional relationship or frontal depth relationship between the scanning unit (gantry 100) and the object can be easily understood by the operator. The viewing direction of the perspective view may be the right direction or may be the left direction. All of the body position setting images 3A to 3H shown in FIG. 6 are perspective views (viewing direction: right) when the operator views the object from the right direction.

The system controller 21 of the medical image diagnostic apparatus 1 reads a body position setting image of a body position pattern selected by the operator from the storage device 213, and displays the body position setting image in the body position setting area 301 (step S102). In a state in which no body position is set, a body position setting image of a body position pattern set in advance as an initial display is displayed. For example, the body position setting image 3A of "head first/supine" shown in FIG. 7(*a*) is displayed. The system controller 21 may display the body position pattern, which is displayed in the body position setting area 301, as text in the body position display area 304.

The system controller 21 displays the reference part selection objects 5*a* to 5*h* within the body position setting image 3A displayed in the body position setting area 301, and controls the operation for an operation on each of the objects 5*a* to 5*h* (step S103). As described above, it is preferable that the reference part is, for example, a head (face). When the head (face) is set as a reference part, it is easy to intuitively understand directions, such as left, right, top, and bottom. One of the reference part selection objects 5*a* to 5*h* is always in a selection state. In the selection state, "selected" is displayed. For example, it is preferable to indicate "selected" by lighting up a mark indicating the object or by color change, graphical change of a mark, or the like.

In the example shown in FIG. 7(*a*), the reference part selection objects 5*a*, 5*b*, 5*c*, and 5*d* are displayed on a side close to the gantry 100, and the reference part selection objects 5*e*, 5*f*, 5*g*, and 5*h* are displayed on a side far from the gantry 100. Each reference part selection object is disposed at a position directly facing the front of the face, which is a reference part, in each body position pattern. In the initial state, a body position pattern "headfirst/supine", in which the face that is a reference part faces upward on the gantry 100 side, is set. Among the eight reference part selection objects, the reference part selection object 5*a* displayed on the gantry side/on the gantry is in a "selected" display state.

In addition, the system controller 21 may display an arrow 305 indicating the direction of scanning together with the body position setting images 3A to 3H. The arrow 305 indicating the direction of scanning may indicate a direction in which the bed moves during the scanning, or may indicate a direction in which X-ray transmission data for the object is obtained. Preferably, the direction to be indicated is selectable in advance by the setting of the operator.

When one of the reference part selection objects is selected by the mouse 108 or the like (step S104; Yes), the system controller 21 switches the display of "selected"/"not selected" of the reference part selection object (step S105). Then, the system controller 21 reads a body position setting image corresponding to the position and direction indicated by the selected object from the storage device 213, and displays the read body position setting image by switching the currently displayed body position setting image to the read body position setting image (step S106). Then, the system controller 21 displays the selected body position as text in the body position display area 304 (step S107). Then, the body position and direction of the object are set as scanning conditions (step S108).

FIG. 7(*b*) shows the body position setting image 3H after selecting the body position.

In the body position setting image 3A shown in FIG. 7(*a*), when the reference part selection object 5*h* is selected through the mouse operation of the operator, the system controller 21 sets the display of the reference part selection object 5*a*, which has been in a non-selection state, to the display state indicating "not selected". Then, the system controller 21 changes the display of the selected reference part selection object 5*h* to the display state indicating "selected". The system controller 21 reads the body position setting image 3H corresponding to the selected reference part selection object 5*h* from the storage device 213. In the example shown in FIG. 7(*b*), the body position corresponding to the selected reference part selection object 5*h* is "feet first/lying on the left side". The system controller 21 reads the body position setting image 3H indicating "feet first/lying on the left side" from the storage device 213, and displays the body position setting image 3H by switching the image.

When the direction of scanning is changed by the operation from the input device 109, the system controller 21 also changes the direction of the arrow 305.

After the setting of the body position ends, the process returns to step S104. When there is another operation of selecting the reference part selection object, steps S105 to S108 are repeated.

When the object information is input to the object information input area 302 (step S109; Yes), the system controller 21 performs processing for registering the input object information (step S110). In addition, when the part of the examination or the examination content is input to the examination content setting area 303 (step S111; Yes), the system controller 21 performs registration processing with the input examination information as scanning conditions (step S112).

When the setting of the body position and the like ends and a scanning operation is performed in the input device 109, scanning is performed under the set scanning conditions in the medical image diagnostic apparatus 1. After the scanning ends, the medical image diagnostic apparatus 1 releases the body position setting, takes the bed out from the gantry, and guides the object out.

As described above, in the first embodiment, reference part selection objects indicating the position and direction of the reference part of the object are displayed at a plurality of positions together with the body position setting image showing the positional relationship between the scanning unit and the object. Thus, when one of the reference part selection objects is selected, a body position corresponding to the selected object is set as scanning conditions. In addition, a body position setting image corresponding to the selected object is displayed by being switched.

By adopting such a body position setting method, the operator can intuitively set the body position. Since the setting of both the body position and the direction can be performed with a single click, the operation is easy. In addition, since it is sufficient to display one body position setting image without arranging a plurality of images, it is possible to perform an operation on a relatively large image even within the screen having a limited display area.

Although an example is shown in which the above-described body position setting image is displayed on the display device 107 provided in the operating console 20 in the operating room, the present invention is not limited thereto. For example, in a medical image diagnostic apparatus in which a separate display device is provided in the scanning unit 10 (gantry 100 or the like) provided in the scanning room, the body position setting image or the reference part selection object may also be displayed on the separate display device.

In addition, it is preferable to be able to change the viewing direction of the body position setting image so as to match the viewing direction when the operator actually sees the scanning unit 10 from the standing position. For example, although the scanning unit in the body position setting image (gantry 100) is drawn on the left side of the bed (viewing direction: right) in the example shown in FIG. 7, the viewing direction of the image is not limited thereto. A body position setting image in which the scanning unit is seen on the right side of the bed (viewing direction: left) may be stored for each body position, and a body position setting image matching the positional relationship between the scanning unit and the bed that the operator actually sees may be displayed.

In addition, a switching operation unit for displaying a body position setting image with a switched point of view may be provided within the scanning condition setting screen 300 or near the display device.

In addition, although "supine", "prone", "lying on the right side", and "lying on the left side" have been described as examples of body positions, a body position, such as tilting slightly to the right (or left) may also be included. However, the display of too many choices makes an image complicated, and this makes an operation difficult rather. Therefore, it is preferable to present several optimal body positions according to the examined part or the purpose.

Second Embodiment

Next, a second embodiment of the present invention will be described with reference to FIGS. 8 to 10.

In the second embodiment, a body position setting method that is suitable for performing scanning when the object is in a standing position without using a bed device, for example, as in an X-ray image diagnostic apparatus (X-ray apparatus), will be described. In addition, the same components as the components described in the first embodiment are denoted by the same reference numerals, and repetitive explanation thereof will be omitted.

Figure 8:
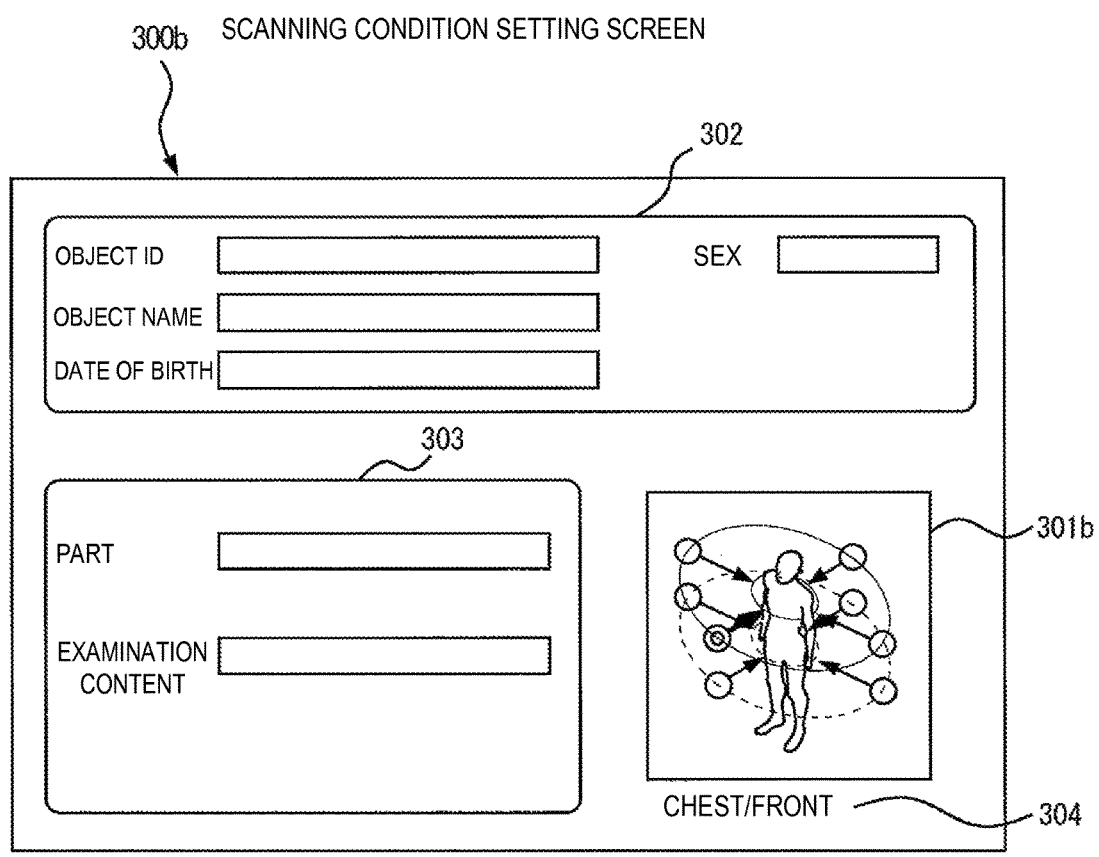
FIG. 8 is an example of a scanning condition setting screen 300b (second embodiment).

FIG. 8 is an example of a scanning condition setting screen 300b of the second embodiment.

A body position setting area 301b, the object information input area 302, and the examination content setting area 303 are provided on the scanning condition setting screen 300b. In addition, a body position display area 304 where the selected body position is displayed as text may be provided near the body position setting area 301b.

The scanning condition setting screen 300b of the second embodiment is different from the scanning condition setting screen 300 of the first embodiment in that a bed is not drawn in the body position setting image displayed in the body position setting area 301b. An object in a standing position is drawn. In the second embodiment, the term "body position" is used to mean the position of the X-ray tube with respect to the object. In other words, the body position referred to in the second embodiment is a scanning part and a scanning direction. The scanning part is each part of the body, such as the head, neck, chest, abdomen, and leg, and the scanning direction is each direction of the object, such as back and forth and left and right. Reference part selection objects 6a to 6h (refer to FIG. 9) are disposed at a plurality of positions that the reference part (X-ray tube) of the scanning unit 10 can take. One of the reference part selection objects 6a to 6h is always in a selection state.

In the second embodiment, since a body position setting image showing the arrangement of apart (reference part; X-ray tube) of the scanning unit with respect to the object is used, one body position setting image may be stored in the storage device 213. That is, a perspective view in which a standing object is drawn is stored as one body position setting image 3. However, a plurality of perspective views having different viewing positions may be stored. In this case, it is preferable to be able to select and display the direction of the object in the image according to the actual position of the object when viewed with the console (position where the operator operates a setting screen).

Next, a body position setting method of the medical image diagnostic apparatus 1 of the second embodiment will be described with reference to FIGS. 9 and 10.

Figure 10:
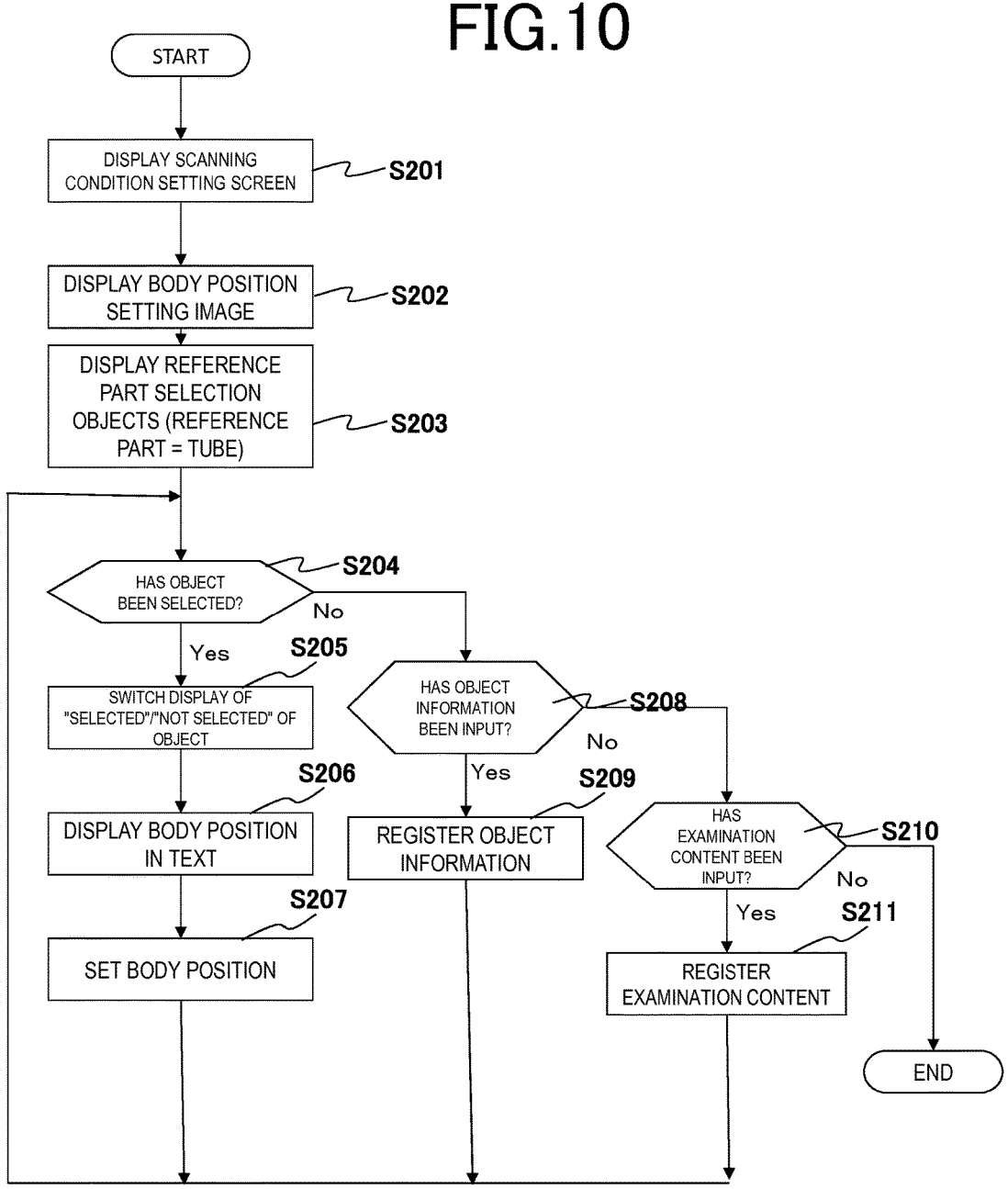
FIG. 10 is a flowchart showing the flow of the body position setting process (second embodiment).

The procedure of steps S201 to S204 in the flowchart of FIG. 10 is the same as that of steps S101 to S104 in the first embodiment (FIG. 4). However, the body position setting image is a body position setting image 3 of the standing position shown in FIG. 9.

As shown in FIG. 9, the body position setting image 3 is drawn with the object in a standing position, and the line (61a and 61b in FIG. 9) showing the height of the scanning part (that is, the height of the tube) is drawn around the object.

In the example shown in FIG. 9, it is assumed that the line 61a shows the height of the chest and the line 61b shows the height of the abdomen. The system controller 21 of the medical image diagnostic apparatus 1 reads the body position setting image 3 from the storage device 213, and displays the body position setting image 3 in the body position setting area 301b (step S202).

The system controller 21 displays the reference part selection objects 6a to 6h.

As shown in FIG. 9, the reference part selection objects 6a to 6h are disposed at the positions of X-ray tubes with respect to the object. In the initial state, for example, as shown in FIG. 9(a), "chest/front" is selected. The line 61a including the selected object may be shown as a solid line, and the other line 61b may be shown as a dotted line. The system controller 21 may display the body position pattern, which is displayed in the body position setting area 301b, as text in the body position display area 304.

When one of the reference part selection objects is selected with the mouse 108 or the like (step S204; Yes), the system controller 21 switches the display showing "selected"/"not selected" of the reference part selection object (step S205). Then, the system controller 21 displays the selected body position in the body position display area 304 (step S206). The selected body position is set as a scanning condition (step S207).

FIG. 9 (b) shows a display state of a body position setting image after body position selection.

In the display state shown in FIG. 9(a), when a reference part selection object 6f is selected through the mouse operation of the operator, the system controller 21 sets the display of the reference part selection object 6a, which has been in a non-selection state, to the display state indicating "not selected". Then, the system controller 21 changes the display of the selected reference part selection object 6f to the display state indicating "selected" as shown in FIG. 9 (b). In addition, the system controller 21 changes the display state of the line 61a to "not selected" and the display state of the line 61b to "selected". Only the display states of the reference part selection objects 6a and 6f and the lines 61a and 61b are changed while maintaining the direction of the object in the body position setting image to be unchanged. In FIG. 9(b), since the reference part selection object 6f is selected, the position of the object is set to "abdomen/left".

After the setting of the body position ends, the process returns to step S204. When there is another operation of selecting the reference part selection object, steps S205 to S207 are repeated.

Since the processing from step S208 is the same as the processing from step S109 in FIG. 4, explanation thereof will be omitted.

As described above, in the second embodiment, the body position setting image 3 including a standing object is used. The reference part of the reference part selection object is assumed to be a part (for example, an X-ray tube) of the scanning unit 10. When a reference part selection object at a certain position, among the reference part selection objects disposed around the object, is selected, the system controller 21 changes the display state of "selected"/"not selected" of the object and sets the body position corresponding to the selected object as a scanning condition.

By adopting such a body position setting method, the operator can intuitively set the body position (scanning part and scanning direction). Since the position of the X-ray tube with respect to the object can be designated as a body position from a plurality of reference part selection objects, it is possible to perform the setting of both the scanning part and the scanning direction with a single click. In addition, since it is sufficient to display one body position setting image at all times, it is possible to perform an operation in a relatively large image even within the setting screen having a limited display area.

Also in the second embodiment, the body position setting image and the reference part selection objects may be displayed on the console in the operating room, or may be displayed on a second display device installed in the scanning unit in the scanning room, as in the first embodiment.

In addition, the viewing direction of the body position setting image may also be changed so as to match the viewing direction when the operator actually sees the scanning unit from the standing position. In addition, a switching operation unit for displaying a body position setting image with a switched viewing direction may be provided within the scanning condition setting screen 300b.

Third Embodiment

Next, a third embodiment of the present invention will be described with reference to FIGS. 11 to 14.

In the third embodiment, a body position setting method suitable for a medical image diagnostic apparatus in which a plurality of body axis directions can be used, such as an open type MRI apparatus, as another form of the medical image diagnostic apparatus 1, will be described.

Figure 11:
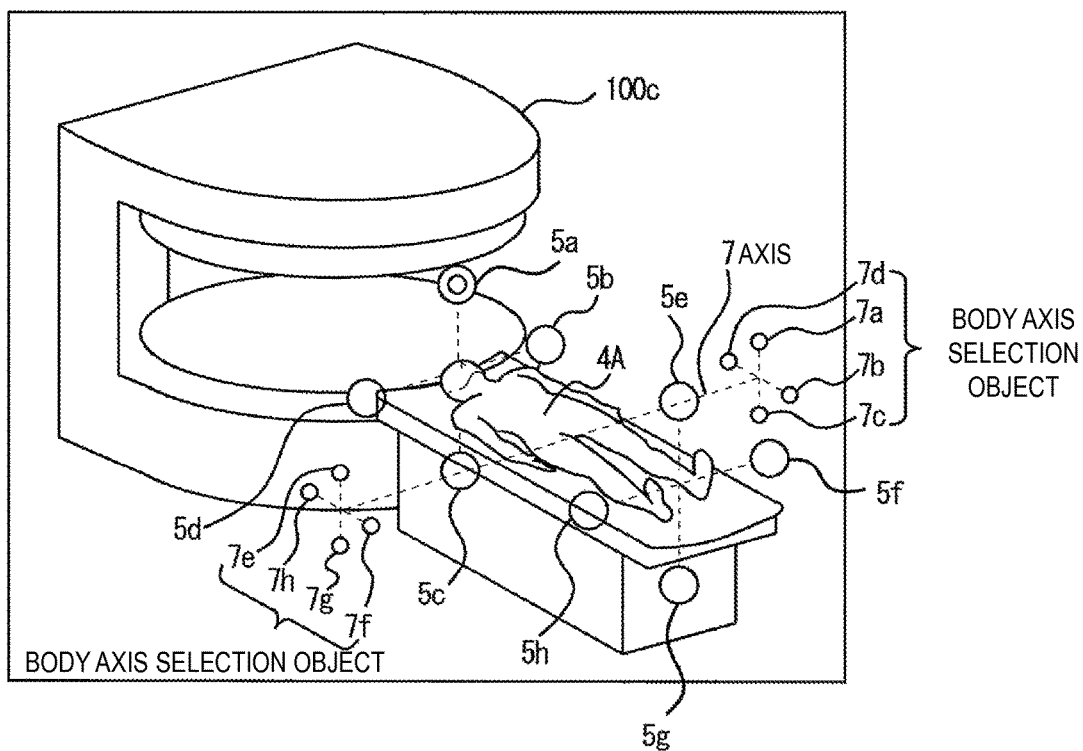
FIG. 11 is an initial display example of a body position setting area 301c of a scanning condition setting screen 300c (third embodiment).
Figure 12:
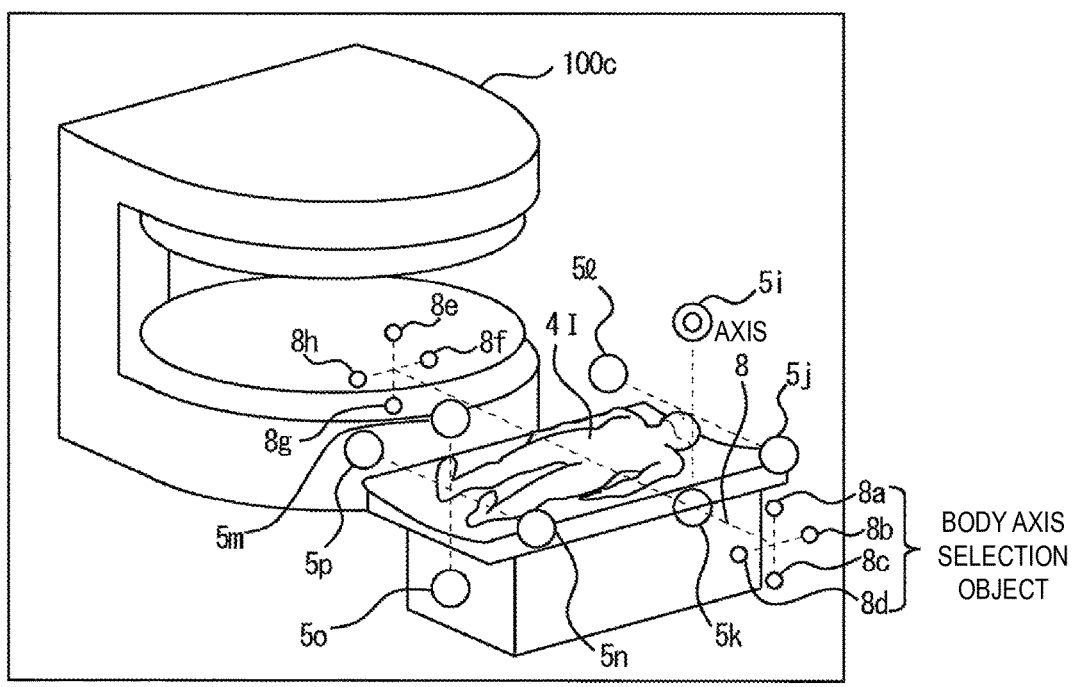
FIG. 12 is a display example of the body position setting area 301c after selecting a body axis selection object (third embodiment).

FIGS. 11 and 12 are diagrams showing examples of bed arrangement in the open type MRI apparatus.

In the open type MRI apparatus, a gantry 100c is divided into up and down portions to form an open scanning space. Therefore, it is possible to use a larger number of body positions. For example, the object is carried so that the body axis of the object is a vertical direction with respect to the scanning space as shown in FIG. 11, or the object is carried so that the body axis is a horizontal direction as shown in FIG. 12. For each body axis direction, there are two head positions and body positions, such as supine, prone, lying on the right side, and lying on the left side.

In the third embodiment, in addition to the reference part selection objects 5a to 5h shown in the first embodiment, body axis selection objects (7 and 7a to 7h in FIGS. 11, 8 and 8a to 8h in FIG. 12) in which the direction of the body axis can also be selected are displayed on the body position selection image.

The body axis selection object is configured to include an axis 7 (axis 8 in FIG. 12) indicating the direction of the body axis and a plurality of marks 7a to 7h (marks 8a to 8h in FIG. 12) disposed at positions for designating the positions and directions of reference parts. When one of the plurality of marks of the body axis selection object is selected, the system controller reads a body position setting image of the body axis and body position corresponding to the selected mark from the storage device 213 and displays the body position setting image.

In the storage device 213, in addition to the body position setting images 3A to 3H of the first embodiment, body position setting images having different body axis directions of the object are stored for each body position.

Figure 13:
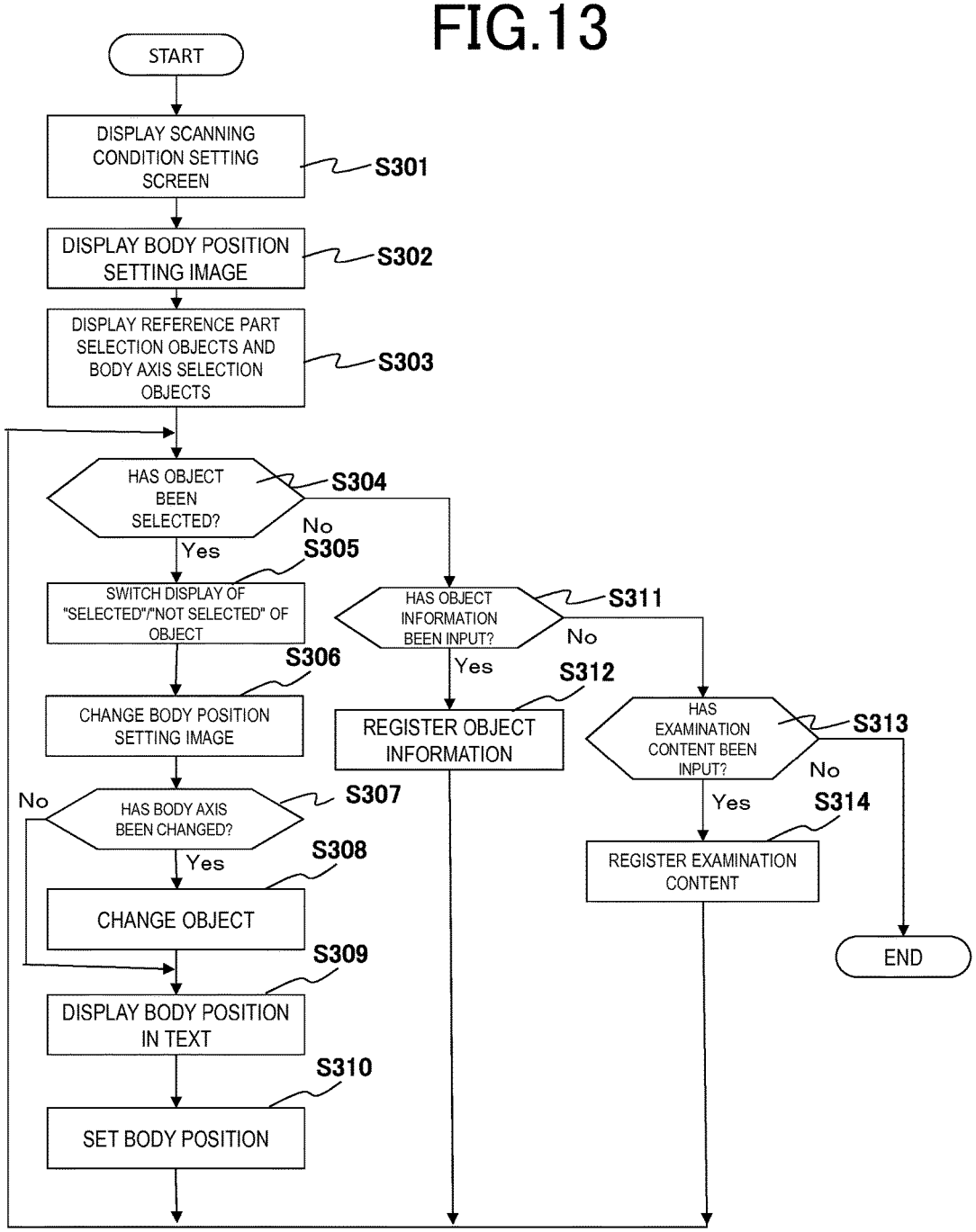
FIG. 13 is a flowchart showing the flow of the body position setting process (third embodiment).

Next, a body position setting method of the medical image diagnostic apparatus 1 of the third embodiment will be described with reference to FIGS. 13 and 14.

The system controller 21 displays a scanning condition setting screen 300c on the display device 107 (step S301). FIG. 14 is an example of the scanning condition setting screen 300c of the third embodiment. The scanning condition setting screen 300c of the third embodiment is different from the scanning condition setting screen 300 (FIG. 5) of the first embodiment in that the scanning unit of a body position setting image displayed in a body position setting area 301c is an open type apparatus and a body axis selection object to select the object body axis is displayed. An object placed on the bed is drawn.

The system controller 21 reads a body position setting image of a body position pattern selected by the operator from the storage device 213, and displays the body position setting image in the body position setting area 301c (step S302). In a state in which no body position is set, a body position setting image of a body position pattern set in advance as an initial display is displayed. For example, as shown in FIG. 11, a body position setting image 4A of body axis direction "vertical" and "head first/supine" is displayed.

The system controller 21 may display the body position pattern, which is displayed in the body position setting area 301c, as text in the body position display area 304.

The system controller 21 displays the reference part selection objects 5a to 5h within the body position setting image 4A displayed in the body position setting area 301c, and controls the operation for an operation on each of the objects 5a to 5h. In addition, the system controller 21 displays the axis 7 and the marks 7a to 7h of the body axis selection object in an axial direction that is different from the body axis direction of the object drawn in the body position setting image 4A, and monitors the operation on the marks 7a to 7h (step S303). In the example shown in FIG. 11, since the body axis direction of the object drawn in the body position setting image 4A is a vertical direction, the body axis selection objects 7 and 7a to 7h having the axis 7 in a different direction (horizontal direction) from the vertical direction are displayed.

When one of the marks 7a to 7h of the reference part selection objects 5a to 5h and the body axis selection objects of the body position setting image 4A is selected through the mouse operation of the operator or the like (step S304; Yes), the system controller 21 sets the display of the object, which has been in a non-selection state, to the display state indicating "not selected". Then, the system controller 21 changes the display of the selected object to the display state indicating "selected" (step S305). Then, the system controller 21 reads the body position setting image corresponding to the selected object from the storage device 213 and performs display switching (step S306).

When the object selected in step S304 is a body axis selection object (step S307; Yes), the body axis of the object in the body position setting image is changed. Therefore, the system controller 21 changes the reference part selection object and the body axis selection object (step S308).

In the body position setting image 4A shown in FIG. 11, when the mark 7a of the body axis selection object is selected, switching to the display state shown in FIG. 12 is performed. In FIG. 12, a body position setting image 4I is displayed in which the body axis direction is a horizontal direction, the reference part of the object is on the right side with respect to the scanning unit, and the supine body position is shown. The system controller 21 switches the arrangement of the reference part selection objects to the positions of reference numerals 5i to 5p. In addition, as body axis selection objects, body axis selection objects (axis 8 and marks 8a to 8h) having the axis 8 in the vertical direction are displayed on the body position setting image 4I.

Then, the system controller 21 displays the selected body position in the body position display area 304 (step S309). Then, the body position and direction of the object are set as scanning conditions (step S310).

After the setting of the body position ends, the process returns to step S304. When there is another object selection operation, steps S305 to S310 are repeated.

Since the processing from step S311 is the same as the processing from step S109 in FIG. 4, explanation thereof will be omitted.

As described above, in the third embodiment, when the body axis of the object can take a plurality of directions with respect to the scanning unit 10, body axis selection objects in which the body positions of different body axis directions can be selected are displayed. Therefore, as in the open type MRI apparatus, also in the scanning unit that can take a plurality of body axis directions in the scanning space, the operator can intuitively understand the body position and set the body position easily. Since each body axis selection object includes marks (7a to 7h and 8a to 8h) used to select the reference part of the body axis, it is possible to select the body axis direction and the body position simultaneously with a single click. In addition, since it is sufficient to display one body position setting image at all times, it is possible to perform an operation in a relatively large image even within the setting screen having a limited display area.

Although the case has been described in which the body axis direction is two directions of the vertical and horizontal directions, the body axis direction may be three or more directions without being limited thereto. However, the display of too many choices makes an image complicated, and this makes an operation difficult on the contrary. Therefore, it is preferable to present one or two optimal body axis directions according to the examined part or the purpose.

Also in the third embodiment, the body position setting image and the reference part selection objects may be displayed on the console in the operating room, or may be displayed on another display device installed in the scanning unit in the scanning room, as in the first and second embodiments.

In addition, the viewing direction of the body position setting image may also be changed so as to match the viewing direction when the operator actually sees the scanning unit from the standing position. In addition, a switching operation unit for displaying a body position setting image with a switched viewing direction may be provided within the scanning condition setting screen 300c or near the display device.

Although the preferred embodiments of the medical image diagnostic apparatus according to the present invention have been described with reference to the accompanying diagrams, the present invention is not limited to such examples. It is apparent to those skilled in the art that various changes and modifications can be made within the range of the technical idea disclosed in this specification, and it should undoubtedly be understood that they also belong to the technical scope of the present invention.

REFERENCE SIGNS LIST

1: medical image diagnostic apparatus
10: scanning unit
100: gantry
101: bed
20: console
21: system controller
107: display device
108: mouse
109: input device
210: CPU
211: main memory
213: storage device
214: communication I/F
215: display memory
216: I/F
107: display device
108: mouse
109: input device
31: display control unit
32: GUI control unit
33: body position setting unit
40: scanning conditions
300, 300b, 300c: scanning condition setting screen
301, 301b, 301c: body position setting area
304: body position display area
5a to 5p: reference part selection object (first and third embodiments)
6a to 6h: reference part selection object (second embodiment)
61a, 61b: height of scanning part
7, 7a to 7h: body axis selection object
8, 8a to 8h: body axis selection object

The invention claimed is:

1. A medical image diagnostic apparatus, comprising:
a console including a processor and a storage device; and
a scanning apparatus; wherein
the console is configured to accept input of and display scanning conditions inputted via an input device, the scanning conditions for use in performing a scanning operation on a body;
the scanning apparatus is configured to scan the body according to the scanning conditions;
the storage device is configured to store plural body position setting images which show images of differing body positions and facing-directions of the body, respectively, together with a positional relationship of the body with the scanning apparatus; and
the processor is configured to:
collect measurement data acquired by the scanning apparatus, and generate a medical image based on the measurement data;
display one body position setting image of the plural body position setting images stored in the storage device, to show one body position and facing-direction of the body on a display device;
monitor a plurality of reference part selection objects displayed around the one body position setting image on the display device, each individual reference part selection object being selectable for selecting a position and direction of a reference part of the body in the one body position setting image, and accepts input of an instruction via the input device to select one of the reference part selection objects as a selected reference part selection object; and
set a selected body position and facing-direction of the body as one of the scanning conditions, according to the selected reference part selection object selected through the input device.

2. The medical image diagnostic apparatus according to claim 1, wherein the processor is configured to:
read a corresponding body position setting image which corresponds to the position and direction of the selected reference part selection object selected through the input unit, from the storage device, and display the corresponding body position setting image by switching the one body position setting image displayed on the display device to the corresponding body position setting image.

3. The medical image diagnostic apparatus according to claim 1,
wherein the one body position setting image is a perspective view.

4. The medical image diagnostic apparatus according to claim 1,
wherein the reference part is a head of the body.

5. The medical image diagnostic apparatus according to claim 1,
wherein the plural body position setting images showing a representation of the body positioned at a same body position but viewed from different points of view, are stored in the storage device, and
the processor is configured to obtain a corresponding body position setting image which corresponds to a positional relationship between the scanning apparatus and the display device that displays the body position setting images, from the storage device, and displays corresponding body position setting image.

6. The medical image diagnostic apparatus according to claim 5,
wherein the one body position setting image is displayed on the display device provided in the console in an operating room.

7. The medical image diagnostic apparatus according to claim 5,
wherein the one body position setting image is displayed on the display device provided in an examination room having the scanning apparatus.

8. The medical image diagnostic apparatus according to claim 1,
wherein, in the one body position setting image, the body placed on a bed is drawn.

9. The medical image diagnostic apparatus according to claim 1,
wherein, in the one body position setting image, the body in a standing position is drawn.

10. The medical image diagnostic apparatus according to claim 1,
wherein the plural body position setting images having different directions of a body axis of the body with respect to the scanning apparatus, are stored in the storage unit, and
the object control unit further displays a body axis selection object for selecting a direction of a body axis in the body position setting image.

11. The medical image diagnostic apparatus according to claim 1,
wherein the facing-directions of the body with respect to the scanning apparatus includes a head-first direction in which a head of the body is placed on a scanning apparatus side, and a feet-first direction in which feet of the body are placed on the scanning apparatus side.

12. A medical image diagnostic apparatus, comprising:
a console including a processor and a storage device; and
a scanning apparatus; wherein
the console is configured to accept input of and display scanning conditions inputted via an input device, the scanning condition for use in performing a scanning operation on a body;
the scanning unit is configured to scan the body according to the scanning conditions;
the storage device is configured to store plural body position setting images which show images of differing body positions and facing-directions of the body, respectively, together with a positional relationship of the body with the scanning apparatus; and
the processor is configured to:
collect measurement data acquired by the scanning apparatus, and generate a medical image based on the measurement data;
display a predetermined initial body position setting image of the plural body position setting images stored in the storage device, to show one body position and facing-direction of the body on a display device;
monitor a plurality of reference part selection objects displayed around the one body position setting image on the display device, each reference part selection object being selectable for simultaneously selecting both a position and direction of a reference part of the body in the one body position setting image, where the object control unit further accepts input of an instruction via the input device to select one of the reference part selection objects as a selected reference part selection object; and set both a selected body position and facing-direction of the body as ones of the scanning conditions, according to the selected reference part selection object selected through the input device.

13. A medical image diagnostic apparatus, comprising:
a console including a processor and a storage device; and
a scanning apparatus; wherein
the console is configured to accept input of and display scanning conditions inputted via an input device, the scanning conditions for use in performing a scanning operation on a body;
the scanning apparatus is configured to scan the body according to the scanning conditions;
the storage device is configured to store plural body position setting images which show images of differing body positions and facing-directions of the body, respectively, together with a positional relationship of the body with the scanning apparatus; and
the processor is configured to:
collect measurement data acquired by the scanning apparatus, and generate a medical image based on the measurement data;
display a predetermined initial body position setting image of the plural body position setting images stored in the storage device, to show one body position and facing-direction of the body on a display device;
monitor a plurality of reference part selection objects displayed around the one body position setting image on the display device, each reference part selection object being selectable for selecting both a position and direction of a reference part of the body at a same time via a single selection, each reference part selection object of the plurality of reference part selection objects for selecting a differing body position and/or facing-direction of the body, respectively, where the object control unit further accepts input of an instruction via the input device to select one of the reference part selection objects as a selected reference part selection object; and
set both a selected body position and facing-direction of the body as ones of the scanning conditions, according to the selected reference part selection object selected through the input device.

* * * * *